United States Patent
Boeve

(10) Patent No.: US 9,451,900 B2
(45) Date of Patent: Sep. 27, 2016

(54) ARRANGEMENT AND METHOD FOR HEATING OF A MAGNETIC MATERIAL

(75) Inventor: Hans Marc Bert Boeve, Hechtel-Eksel (BE)

(73) Assignee: Koninklijke Philips N.V., Eindhoven (NL)

( * ) Notice: Subject to any disclaimer, the term of this patent is extended or adjusted under 35 U.S.C. 154(b) by 1359 days.

(21) Appl. No.: 13/319,351

(22) PCT Filed: Apr. 19, 2010

(86) PCT No.: PCT/IB2010/051699
§ 371 (c)(1),
(2), (4) Date: Nov. 8, 2011

(87) PCT Pub. No.: WO2010/128418
PCT Pub. Date: Nov. 11, 2010

(65) Prior Publication Data
US 2012/0058441 A1 Mar. 8, 2012

(30) Foreign Application Priority Data
May 8, 2009 (EP) .................................... 09159802

(51) Int. Cl.
*A61B 5/05* (2006.01)
*A61N 1/40* (2006.01)
*A61N 2/02* (2006.01)
*G01R 33/12* (2006.01)

(52) U.S. Cl.
CPC ............... *A61B 5/05* (2013.01); *A61B 5/0515* (2013.01); *A61N 1/403* (2013.01); *A61N 2/02* (2013.01); *G01R 33/1276* (2013.01)

(58) Field of Classification Search
CPC ...................................................... C21D 1/04
USPC ........................................................ 148/108
See application file for complete search history.

(56) References Cited

U.S. PATENT DOCUMENTS 6,470,220 B1  10/2002  Kraus, Jr. et al.

FOREIGN PATENT DOCUMENTS

| DE | 10151778 | 5/2003 |
|---|---|---|
| DE | 10238853 | 3/2004 |
| EP | 0913167 | 5/1999 |
| EP | 1304542 | 4/2003 |
| EP | 1738773 | 1/2007 |
| EP | 1738774 | 1/2007 |
| WO | WO2004018039 | 3/2004 |
| WO | WO2004091386 | 10/2004 |
| WO | WO2004091393 | 10/2004 |
| WO | WO2006035359 | 4/2006 |

OTHER PUBLICATIONS

Gleich, B. and Weizenecker, J., "Tomographic Imaging Using the Nonlinear Response of Magnetic Particles", Nature 2005, vol. 435, pp. 1214-1217.

*Primary Examiner* — Jessee Roe
*Assistant Examiner* — Christopher Kessler

(57) ABSTRACT

The present invention relates to an arrangement (10) for heating of a magnetic material (100) located in the center region of an inscribed sphere within a region of action, which arrangement comprises: —selection means (210) for generating a magnetic selection field (211) having a pattern in space of its magnetic field strength such that a first sub-zone (301) having a low magnetic field strength and a second sub-zone (302) having a higher magnetic field strength are formed in the region of action (300), —drive means (220) for changing the position in space of the two sub-zones (301, 302) in the region of action (300) by means of a magnetic drive field (221) so that the magnetization of the magnetic material (100) changes locally, and —control means (76) for controlling the drive means (220) to change the position in space of the first sub-zone (301) along a sequence of locations around said inscribed sphere for so long and with such a frequency that the center region of said inscribed sphere is heated.

10 Claims, 7 Drawing Sheets

ARRANGEMENT AND METHOD FOR HEATING OF A MAGNETIC MATERIAL

FIELD OF THE INVENTION

The present invention relates to an arrangement and a corresponding method for heating of a magnetic material located in the centre region of an inscribed sphere within a region of action. Further, the present invention relates to a computer program.

BACKGROUND OF THE INVENTION

An arrangement of this kind is known from WO 2004/018039 A1, which particularly describes a system and method for the local heating of a target region of an object by varying the magnetization of magnetic or magnetizable substances. A magnetic field is generated whose magnetic field strength varies in space in such a manner that a first sub-region of low magnetic field strength and a second sub-region which encloses the first sub-region and has a higher magnetic field strength are formed in the target region (also called region of action). Subsequently, the position in space of the two sub-regions in the target region is varied with a given frequency for so long that the particles are heated to a desired temperature due to frequent variation of the magnetization.

A so-called Magnetic Particle Imaging (MPI) arrangement and method is known from Gleich, B. and Weizenecker, J. (2005), "Tomographic imaging using the nonlinear response of magnetic particles" in Nature, vol. 435, pp. 1214-1217. The arrangement and method for magnetic particle imaging (MPI) described in that publication takes advantage of the non-linear magnetization curve of small magnetic particles. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement has the advantage that it can be used to examine arbitrary examination objects—e.g. human bodies—in a non-destructive manner and without causing any damage and with a high spatial resolution, both close to the surface and remote from the surface of the examination object.

A number of materials are available that give a good signal in MPI, such as Resovist®. For a magnetic particle to react to an ac magnetic field, different mechanisms may be responsible: (1) Néel rotation in the case of single-domain particles, (2) geometric Brownian rotation, and (3) domain wall movement for multi-domain particles. For MPI, magnetic particles are optimised for the Néel rotation, which allows for a fast response to the external field so that the non-linear magnetization response can be analyzed in a good number of harmonics.

Magnetic hyperthermia stands for a local heating effect that can lead to apoptosis of tumor cells (thermoablation) if the local temperature exceeds the window 42-45° C. In combination with other cancer treatment modalities such as brachytherapy, local moderate heating may result in an increase in efficacy of the combined method. Local heating can be realised due to the presence of magnetic nanoparticles in tumor cells or in close vicinity thereof. Magnetic nanoparticles are usually administered intratumorally.

SUMMARY OF THE INVENTION

It is an object of the present invention to provide an arrangement and a corresponding method for heating of a magnetic material located in the centre region of an inscribed sphere within a region of action, which provide optimized heating conditions which are highly focused on the centre region to be heated.

In a first aspect of the present invention an arrangement for heating of a magnetic material located in the centre region of an inscribed sphere within a region of action is presented that comprises:

selection means for generating a magnetic selection field having a pattern in space of its magnetic field strength such that a first sub-zone having a low magnetic field strength and a second sub-zone having a higher magnetic field strength are formed in the region of action, drive means for changing the position in space of the two sub-zones in the region of action by means of a magnetic drive field so that the magnetization of the magnetic material changes locally, and control means for controlling the drive means to change the position in space of the first sub-zone along a sequence of locations around said inscribed sphere for so long and with such a frequency that the centre region of said inscribed sphere is heated.

In a further aspect of the present invention a corresponding method is presented.

Still further, in another aspect of the present invention a computer program is presented comprising program code means for causing a computer to control an arrangement according to the present invention to carry out the steps of the method according to the present invention when said computer program is carried out on the computer.

Preferred embodiments of the invention are defined in the dependent claims. It shall be understood that the claimed method has similar and/or identical preferred embodiments as the claimed device and as defined in the dependent claims.

The present invention is based on the following considerations and recognitions.

Using magnetic nanoparticles, the specific power loss which is a function of magnetic field frequency and amplitude can be calculated from $P(v,H)=\mu_0 \pi \chi''(v) H^2 v [W/g]$, where $\chi''(v)$ represents the complex part of the susceptibility of the magnetic nanoparticles. The heat generation is a result of two different phenomena:

1. Neel reversal of magnetization inside a magnetic particle (thermal relaxation driven)
2. Brownian rotation of the magnetic particle in a fluid suspension (relative to surroundings)

Typical values used in hyperthermia experiments are: particle size 10-25 nm, frequency 400 kHz, amplitude 10 kA/m An issue of hyperthermia is its compatibility with magnetic particle imaging with an operational base frequency of 25 kHz. A first option is to move to higher frequency to generate more heat per unit time. However this would require MPI to scale to higher frequency which results in a loss of signal generation due to the necessity of a lower effective anisotropy in relevant particles. A second option would be to move to higher amplitude, however it is known that for the frequency range of MPI, i.e. 25 kHz, there is a strong contribution of Brownian motion in the complex susceptibility, which does not increase as soon as a minimal field amplitude threshold is overcome. Moreover, magnetic hyperthermia looses its ability to be a focal technology for too high an amplitude. It is to be noted that 10 mT is the envisioned full field swing in a complete imaging volume. Hence field values should be reduced rather than increased.

In this way it would be possible to expose a point to 'heat' for a longer time. The consequence is two-fold: (1) from a workflow point of view, the treatment time will increase accordingly, and (2) due to heat leakage into neighboring tissue, the focal aspect of heat delivery will fade out, which can only be overcome by operation with a lower duty cycle resulting in an even long treatment time.

The present invention relies primarily on the Brownian rotational degree of freedom of suspended magnetic particles. Given that magnetic particles are delivered intratumorally, a sequence of the spatial positions of the field free point (FFP; corresponds to the first sub-zone having a low magnetic field strength) as a function of time can be defined, that is able to rotate the cumulative magnetic vector in a particular area, in particular in the centre region, in a concerted way. Such a fundamental sequence is revolving around the defined area in which magnetic particles are present and where eventually the heating effect will be focused. Heating power will scale with the revolving frequency of the particles.

Given the Debye time constant for Brownian relaxation in the order of few to tens of kHz, which depends on the hydrodynamic diameter ($\tau=4\pi\eta r^3/kT$), maximum heating power will be generated at a similar revolving particle frequency. An interesting aspect is that the fundamental frequency of MPI is in the same order, i.e. 25 kHz.

Thus, according to the present invention a family of revolving focal heating sequences (in particular for MPI, whereby receiving means for signal detection and processing means for image generation from said detection signals are not necessarily required) are proposed that allow for a very local heating, for instance for focal cancer therapy.

A revolving sequence is defined as the spatial position of the field free point as function of time. Suppose that this position is located on a sphere with the magnetic material in its origin. In 3D space the field free point 'spins' around the magnetic material in a fashion comparable to an electron spinning around its nucleus. Due to the fact that the magnetic material is now exposed to a constant magnetic field that is continuously changing its direction, i.e. in the direction opposite to the field free point, the magnetization vector will (try to) align to this field. The effective magnetic field strength is a function of the gradient field in MPI and the radius of the revolving sphere.

In a competition between Neel internal realignment and Brownian particle rotation, both degrees of freedom may be excited. It is well established that larger magnetic core sizes have a tendency to favour Brownian particle rotation due to frustration of the magnetization vector within the lattice due to a high anisotropy, disallowing Neel internal realignment within the time frame of the measurement (loss of superparamagnetism). As a result the most efficient heat generation mechanism can be excited maximally.

In preferred embodiments magnetic particle assays are optimised to favour Brownian particle rotation, either from chemical synthesis or physical fractionation. This is preferably achieved by nanoparticles that are thermally blocked. The way to look at this is as follows: superparamagnetism is the fundamental effect behind e.g. MRI contrast agents.

If the magnetic core diameter and/or magnetic anisotropy increases, which is physically equivalent to an increase of the "energy" equal to the product K.V to be compared to the thermal energy k.T, the magnetization may become thermally blocked. In fact, this means that Neel internal realignment is no longer possible and Brownian rotation will dominate (provided that the frequency range of operation matches this fundamental frequency ~kHz). For Fe oxide particles this transition usually takes place around 20 to 40 nm. Assays of larger particles can be produced, as well as assays with a substantial polydispersity, i.e. with an important fraction of larger particles.

As a result, according to the present invention MPI has been turned into an excellent method to provide and focus optimal heating conditions locally by revolving sequence design. This prevents a high degree of fractionation in the treatment to be delivered, which is essential for optimal workflow.

According to a preferred embodiment the control means is adapted for controlling the drive means to change the position in space of the first sub-zone along a two-dimensional sequence of locations, in particular along a circle, around said inscribed sphere.

According to an alternative embodiment the control means is adapted for controlling the drive means to change the position in space of the first sub-zone along a three-dimensional sequence of locations, in particular over a sphere, around said inscribed sphere.

One main advantage of a two-dimensional trajectory, preferably in a plane that matches the constellation of the MPI system, is a simple control scheme with only two currents. One main advantage of a three-dimensional trajectory is that the circular revolution can be modulated over the third dimension. As a result, if any magnetic material would be present along the path of the field free point (thus outside of the point of interest, i.e. the origin of that circle/sphere or the tumor) then the reorientation of this material would be effectively duty-cycled so that less heat will be generated outside the point of interest (=tumor).

Preferably, the control means is adapted for controlling the drive means to change the position in space of the first sub-zone with constant angular velocity. This enables a simple implementation. In addition, the magnetization vector would be continuously rotating with constant angular velocity, which leads to optimal heating efficiency.

Further, in an advantageous embodiment the control means is adapted for controlling the drive means to change the position in space of the first sub-zone with a frequency in the range from 1 to 100 kHz, in particular in the range from 10 to 30 kHz. Preferably, frequencies will be used that match MPI imaging so that a system can be switched from imaging mode to heating mode. In the case of rotation mode, the characteristic time constant will be in the order of tens of micro-seconds which limits the frequency to tens of kHz. A frequency in the region of 25 kHz is a good compromise.

According to a preferred embodiment, the presence of the magnetic particles can be imaged or monitored before and/or after the heating experiment by the provision of receiving means for acquiring detection signals and processing means for reconstructing an image, as conventionally provided in an MPI arrangement. Instrumentational aspects such as operational frequency, field gradients and field amplitudes in MPI and hyperthermia treatment can now be comparable, so that all functions can be performed by use of the same arrangement.

Preferred magnetic material comprises monodomain magnetic nanoparticles, in particular colloidally stabilised monodomain magnetic nanoparticles. Further preferred is that the monodomain magnetic nanoparticles, in particular the colloidally stabilised monodomain magnetic nanoparticles, are encapsulated into liposomes, polymerosomes or vesicles having an inner volume of with viscosity equal or similar to that of water separated by a hydrophobic membrane, wherein the magnetic particles are arranged in the inner volume.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
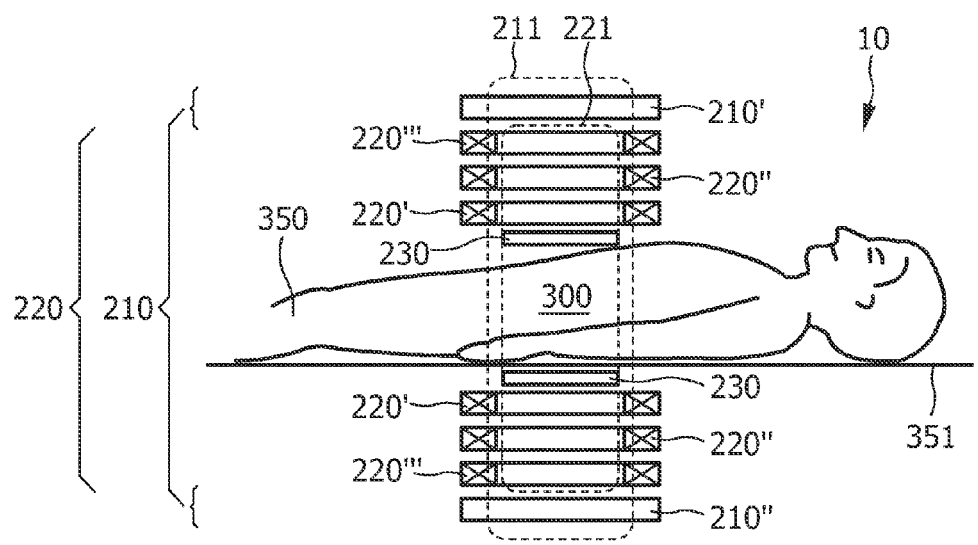
FIG. 1 shows a schematic view of the principle layout of a magnetic particle imaging (MPI) arrangement.

FIG. 1 shows an arbitrary object to be examined by means of a MPI arrangement 10. The reference numeral 350 in FIG. 1 denotes an object, in this case a human or animal patient, who is arranged on a patient table 351, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
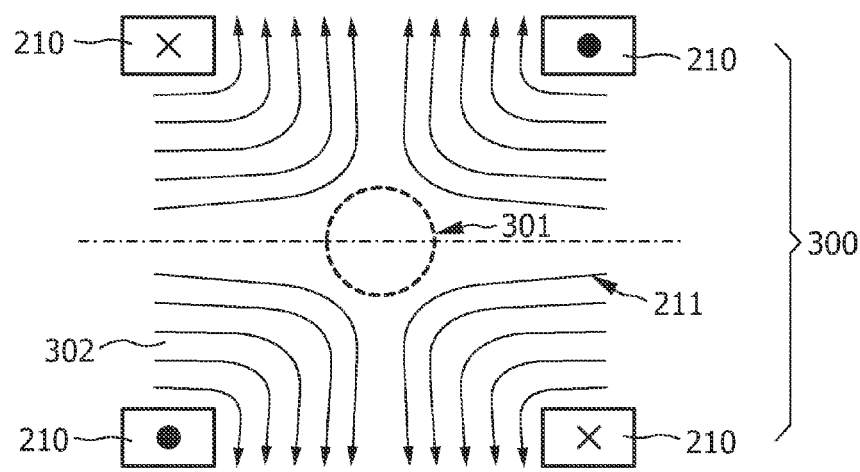
FIG. 2 shows an example of the field line pattern produced by an arrangement according to the present invention.

As an example of an embodiment of the present invention, an arrangement 10 is shown in FIG. 2 comprising a plurality of coils forming a selection means 210 whose range defines the region of action 300 which is also called the region of treatment 300. For example, the selection means 210 is arranged above and below the patient 350 or above and below the table top. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameters influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
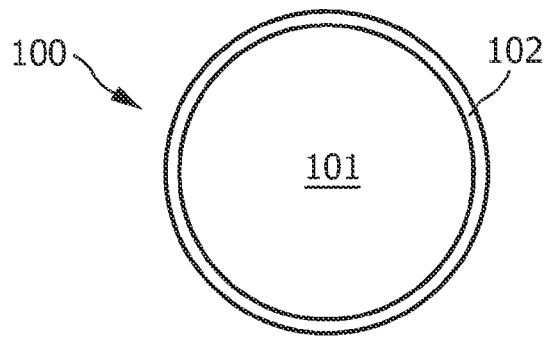
FIG. 3 shows an enlarged view of a magnetic particle present in the region of action.

FIG. 3 shows an example of a magnetic particle 100 of the kind used together with an arrangement 10 of the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

Another suitable material is, for instance, described in EP 1738773 and EP 1738774 where magnetic nanoparticles optimised for MPI have been described, i.e. colloidal Fe oxide based SPIO (i.e. superparamagnetic nanoparticles). Other suitable material comprises monodomain magnetic nanoparticles, in particular colloidally stabilised monodomain magnetic nanoparticles. Further preferred is that the monodomain magnetic nanoparticles, in particular the colloidally stabilised monodomain magnetic nanoparticles, are encapsulated into liposomes, polymersomes or vesicles having an inner volume of with viscosity equal or similar to that of water separated by a hydrophobic membrane, wherein the magnetic particles are arranged in the inner volume.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to 160 $10^3$ A/m2, the first sub-zone 301 in which the magnetization of the particles 100 is not saturated has dimensions of about 1 mm (in the given space direction).

When a further magnetic field—in the following called a magnetic drive field 221—is superposed on the magnetic selection field 210 (or gradient magnetic field 210) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220" and a fourth coil pair 220'" which together are called drive means 220 in the following. For example, the second coil pair 220' generates a component of the magnetic drive field 221 which extends in the direction of the coil axis of the first coil pair 210', 210" or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210", so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220", 220'" are provided in order to generate components of the magnetic drive field 221 which extend in a different direction in space, e.g. horizontally in the longitudinal direction of the region of action 300 (or the patient 350) and in a direction perpendicular thereto. If third and fourth coil pairs 220", 220'" of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220", 220'" are also arranged above and below the region of action 300 and, therefore, their winding configuration must be different from that of the second coil pair 220'. Coils of this kind, however, are known from the field of magnetic resonance apparatus with open magnets (open MRI) in which an radio frequency (RF) coil pair is situated above and below the region of treatment, said RF coil pair being capable of generating a horizontal, temporally variable magnetic field. Therefore, the construction of such coils need not be further elaborated herein.

This embodiment of the arrangement 10 according to the present invention further comprise receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

It shall be noted that such receiving means 230 are not necessarily required to perform the desired method of the present invention. Only, if imaging in addition to the heating of a magnetic material 100 is desired, such receiving means 230 are to be provided in the arrangement.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement according to the present invention, the selection means 210 comprise both at least one permanent magnet and at least one coil 210', 210" as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
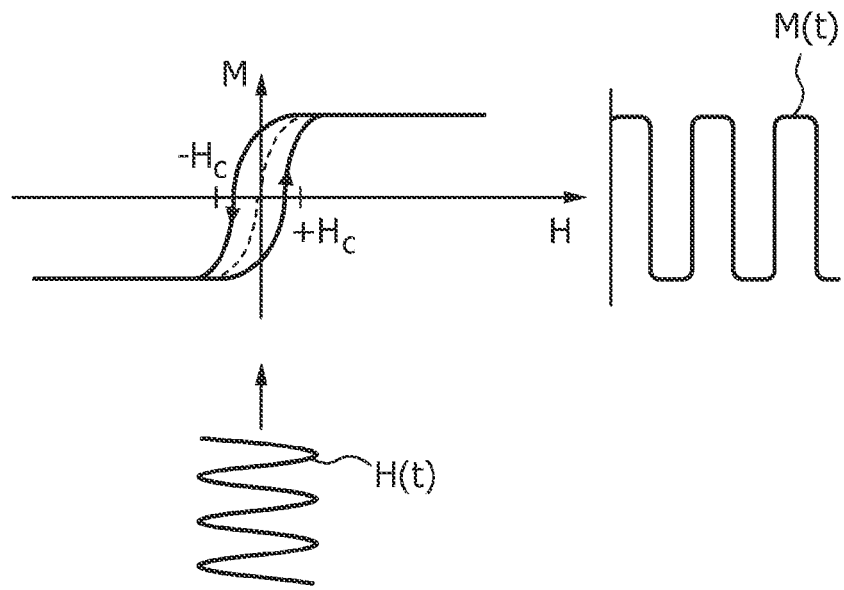
FIGS. 4a and 4b show the magnetization characteristics of such particles.
Figure 4B:
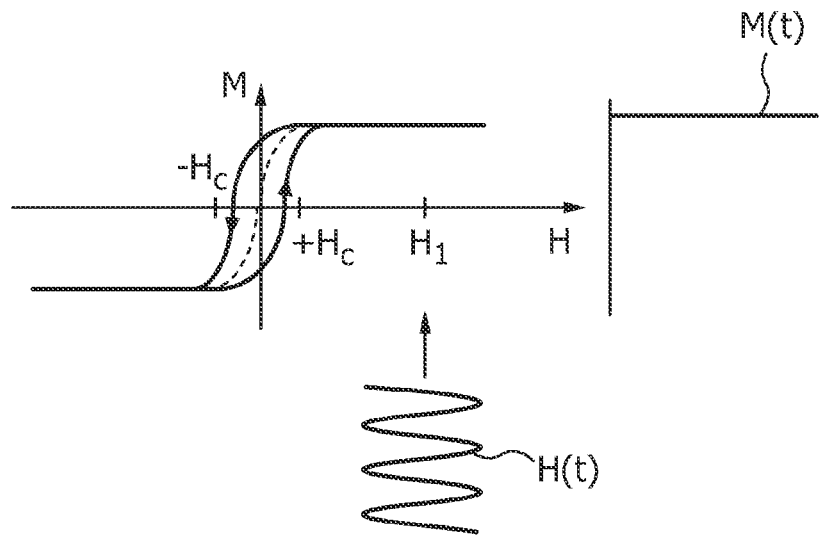

FIGS. 4a and 4b show the magnetization characteristic, that is, the variation of the magnetization M of a particle 100 (not shown in FIGS. 4a and 4b) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4a illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particles 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
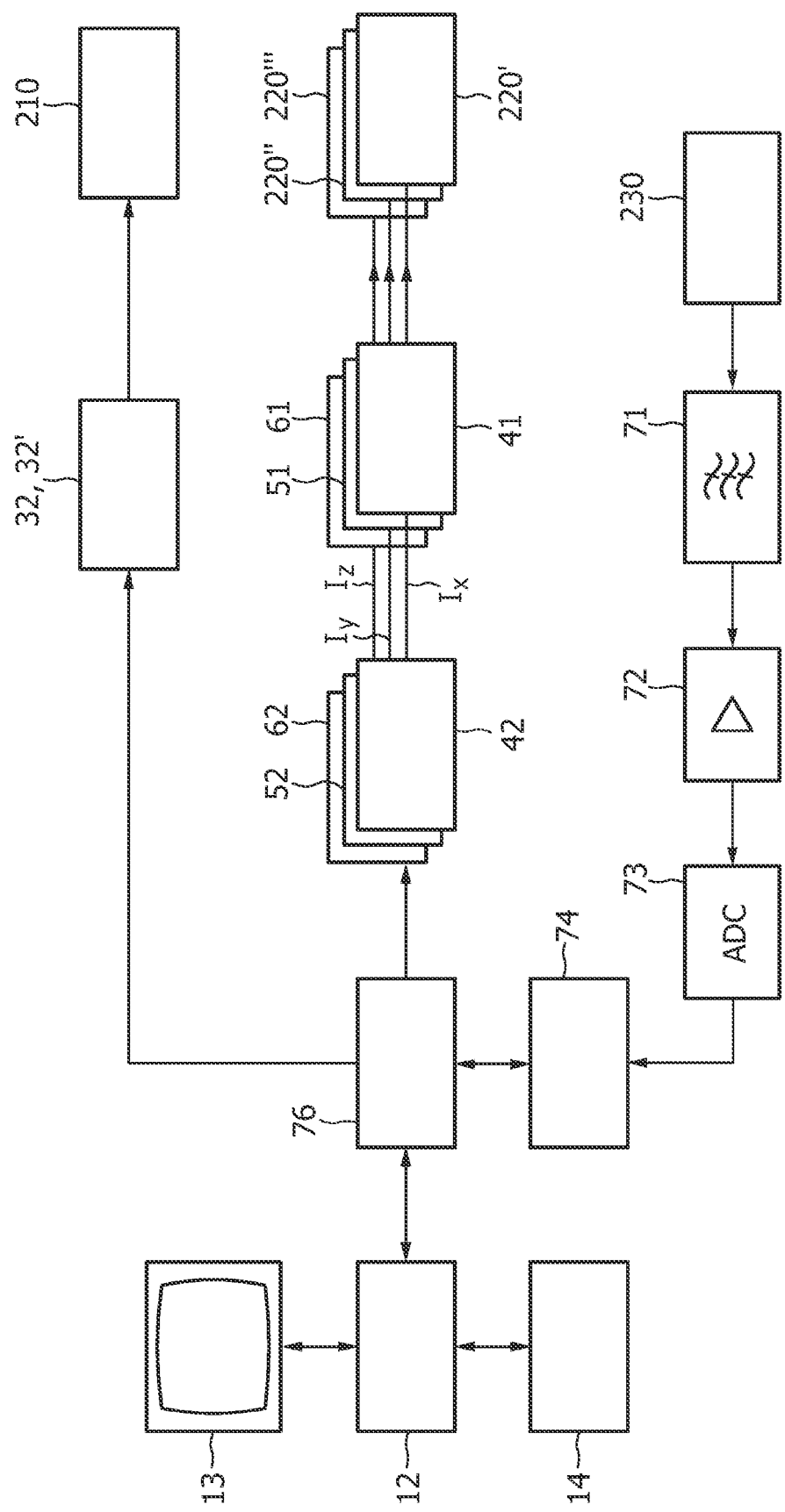
FIG. 5 shows a block diagram of an embodiment of the apparatus according to the present invention.

FIG. 5 shows a block diagram of the apparatus 10 shown in FIG. 1. The selection means 210 is shown schematically in FIG. 5. Preferably, the selection means 210 are provided with three magnetic selection field generation means, in particular either coils, permanent magnets or a combination of coils and permanent magnets. Said three magnetic selection field generation means are preferably arranged such that for each spatial direction one magnetic selection field generation means is provided. If in an embodiment coil pairs are provided as magnetic selection field generation means, the coil pairs are supplied with a DC current from a controllable current source 32, said current source 32 being controlled by the control means 76. In order to individually set the gradient strength of the selection field 211 in a desired direction, an overlaid current is overlaid to at least one of coil pairs, wherein the overlaid current of opposed coils is oppositely oriented. In a preferred embodiment, the control means 76 furthermore controls that the sum of the field strength and the sum of the gradient strength of all three spatial fractions of the selection field 211 is maintained at a predefined level.

If in an embodiment permanent magnets are provided as magnetic selection field generation means instead of coil pairs, the current source 32 need to be exchanged by an actuation means 32', e.g. an electro motor, which is able to mechanically move the permanent magnets in order to set the gradient strength in the desired direction according to the control signals provided by the control means 76.

The control means 76 is in turn connected to a computer 12 which is coupled to a monitor 13 for displaying the distribution of magnetic particles in the examination area and an input unit 14, for example a keyboard. A user is therefore able to set the desired direction of the highest resolution and in turn receives the respective image of the region of action on the monitor 13. If the critical direction, in which the highest resolution is needed, deviates from the direction set first by the user, the user can still vary the direction manually in order to produce a further image with an improved imaging resolution. This resolution improvement process can also be operated automatically by the control means 76 and the computer 12. The control means 76 in this embodiment sets the gradient field in a first direction which is automatically estimated or set as start value by the user. The direction of the gradient field is then varied stepwise until the resolution of the thereby received images, which are compared by the computer 12, is maximal, respectively not improved anymore. The most critical direction can therefore be found respectively adapted automatically in order to receive the highest possible resolution.

The coil pairs (second magnetic means) 220', 220", 220''' are connected to current amplifiers 41, 51, 61, from which they receive their currents. The current amplifiers 41, 51, 61 are in turn in each case connected to an AC current source 42, 52, 62 which defines the temporal course of the currents Ix, Iy, Iz to be amplified. The AC current sources 42, 52, 62 are controlled by the control means 76.

The—not necessarily required—receiving coil (receiving means) is also shown schematically in FIG. 5. The signals induced in the receiving coil 230 are fed to a filter unit 71, by means of which the signals are filtered. The aim of this filtering is to separate measured values, which are caused by the magnetization in the examination area which is influenced by the change in position of the two part-regions (301, 302), from other, interfering signals. To this end, the filter unit 71 may be designed for example such that signals which have temporal frequencies that are smaller than the temporal frequencies with which the coil pairs 220', 220", 220''' are operated, or smaller than twice these temporal frequencies, do not pass the filter unit 71. The signals are then transmitted via an amplifier unit 72 to an analog/digital converter 73 (ADC). The digitalized signals produced by the analog/digital converter 73 are fed to an image processing unit (also called reconstruction means) 74, which reconstructs the spatial distribution of the magnetic particles from these signals and the respective position which the first part-region 301 of the first magnetic field in the examination area assumed during receipt of the respective signal and which the image processing unit 74 obtains from the control means 76. The reconstructed spatial distribution of the magnetic particles is finally transmitted via the control means 76 to the computer 12, which displays it on the monitor 13.

In WO 2004/018039 A such an arrangement (without receiving means) has been described for the application of local heating or regions of an object. It is particularly described therein that, when the position in space of the first sub-region is changed slightly, the magnetization changes of those particles which are situated in the first sub-region or which migrate from the first to the second sub-region or vice versa. Because of this change of the magnetization, heat losses occur, for example, due to known hysteresis effects or hysteresis-like effects in the particles or due to the initiation of particle movements, and the temperature of the medium surrounding the particles is heated in a heating region. When the first sub-region of the magnetic field is shifted through the entire target region, the heating region will correspond to the target region. The smaller the first sub-region, the smaller the size of the smallest possible heating region will be.

Because only a comparatively small amount of heat is produced when the magnetization is changed only once, the magnetization must be changed several times. The necessary number of changes, that is, the frequency within a given time interval, and the associated temperature rise of the medium surrounding the particles in the heating region is dependent on the particle concentration, on the production of heat per change (which itself is dependent on the particle structure and the speed of the magnetic reversal), and the dissipation of heat in the regions surrounding the heating region.

With respect to more details of the general aspects of the application of heating reference is made to WO 2004/018039 A, the description of those general aspects being herein incorporated by reference.

Figure 6:
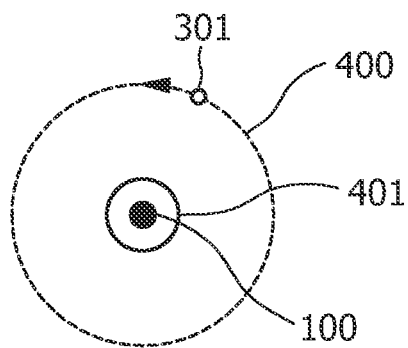
FIG. 6 shows a diagram of an example of a two-dimensional sequence.

The known heating effect mainly exploits the above described Neel effect. In contrast, the present invention relies primarily on the Brownian rotational degree of freedom of suspended magnetic particles. Hence, according to the present invention the control means 76 for controlling the drive means 220 are arranged to change the position in space of the first sub-zone 301 (FFP) along a sequence of locations around an inscribed sphere for so long and with such a frequency that the centre region of said inscribed sphere is heated. This is schematically illustrated in FIG. 6, which shows a two-dimensional continuous revolving sequence 400 of locations of the FFP 301 around the centre region 401 in which, for instance, a tumor is located and in which magnetic material 100 is placed. The inscribed sphere preferably has the same diameter as the circular sequence 400, but can also have a smaller diameter (but no larger diameter).

The revolving sequence 400 is generated as function of time by a selection field with its field free point located at the position of in the magnetic material, superposed with AC fields. The AC fields are orthogonal (90 deg phase shift): Hx=Heff cos(ωt); Hy=Heff cos(ωt+π/2)=Heff sin(ωt), with Heff equal to the product of the gradient selection field and the radius of the revolving circle visualizing the effective time evolution of the field free point.

The combination of frequency and effective field Heff can be optimised according to a particular magnetic particle assay for maximum heat generation. Frequency and effective field can be tuned for maximum heat generation in a particular magnetic particle assay. The other way around, tuning the chemistry to make those particles, would be most difficult. Heat generation scales with the square of the effective field and the frequency, however that complex susceptibility is also a function of frequency and of the time constants of Neel/Brown remagnetisation. Therefore it is anticipated that optimum parameters can be found for every other assay.

It is to be noted that the effective field is set by the gradient fields in the system and the diameter of the inscribing sphere along which the field free point is moved around. This effective field should be as large as possible but will be practically limited to ~5-10-20 mT.

In another embodiment a continuous 3D sequence is used. In this embodiment the revolving sequence ultimately has their field free point located on a sphere but covers the complete sphere in 3D, to be realised with: Hx=Heff cos(ω₁t) cos(ω₂t); Hy=Heff cos(ω₁t) sin(ω₂t); Hz=Heff cos(ω₂t) where ω₁ and ω₂ differ only slightly, e.g. 1%, and with Heff equal to the product of the gradient selection field and the radius of the revolving sphere.

Again, the combination of frequencies and effective field Heff can be optimised according to a particular magnetic particle assay for maximum heat generation. The above comments with respect to the optimization apply here as well.

Figure 7:
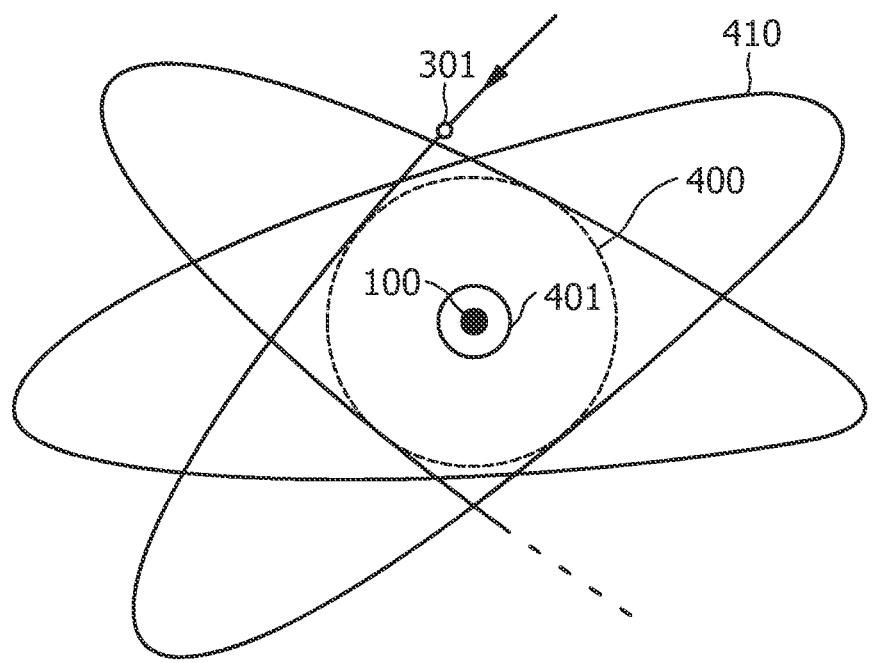
FIG. 7 shows a diagram of an example of a three-dimensional sequence.
Figure 8:
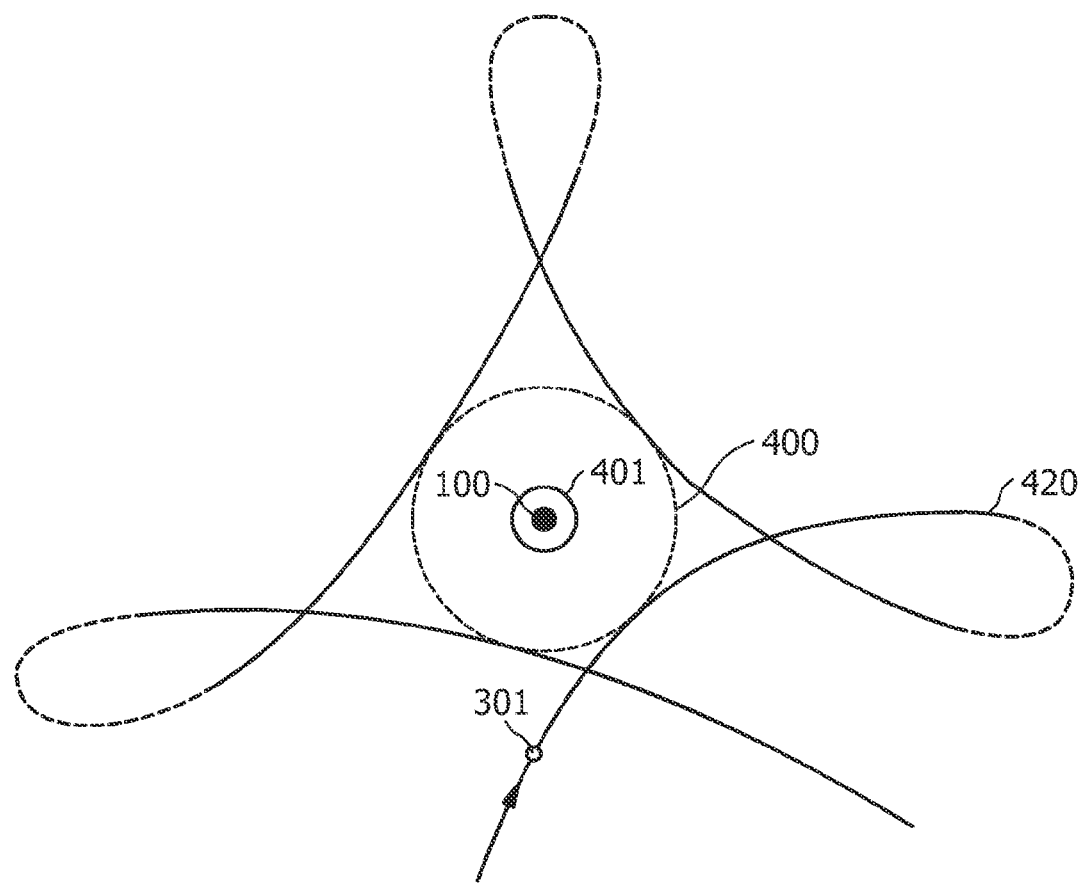
FIG. 8 shows a diagram of another example of a three-dimensional sequence.

More complex sequences can be used in 2D or 3D, as long as the inscribing feature corresponds to a the circle or sphere, respectively. Two examples include parametric 2D and 3D time paths 410, 420 as depicted in FIGS. 7 and 8. The frequencies involved in the parametric path are preferably limited to a couple of base frequencies that only differ slightly (compare to $\omega_1$ and $\omega_2$ mentioned above) as to not complicate design aspects in the instrumentation such as transmit and receive filters. As a result, the effective torque (or more generally speaking manipulation) of the magnetization vector of the magnetic particles 100 in the centre 401 is now modulated by a modulation in effective magnetic field in that location. This degree of freedom gives an additional parameter for optimization of frequency and effective field for maximum heat generation. It is to be noted once more that maximum heat generation is essential to maintain the implicit focus that has been created by the local presence of magnetic material.

Effective duty-cycling as described here may be appropriate for magnetic particle assays that do not entirely match a particular operational frequency for MPI imaging.

Thus, as explained above, the common characteristic of all trajectories is that they comprise an inscribed sphere that is formed around the location of the tumor. As a result the magnetization of any magnetic material in that location will have a revolving character.

Preferably frequencies will be used that match MPI imaging so that a system can be switched from imaging mode to heating mode. In the case of rotation mode, the characteristic time constant will be in the order of tens of micro-second which limits the frequency to tens of kHz. Therefore 25 kHz is a good compromise.

For 2D case of a circle, one would use the same frequency that is offset in phase (π/2).

Polar coordinates r=r; Θ=2πft equals x=r cos(2πf.t); y=r cos(2πf.t+π/2).

For the 3D case of a frequencies are preferably used that match MPI imaging so that a system can be switched easily between imaging and heating mode.

The key to the idea in going from 2D to 3D is to spread any additional heating effects on the circular trajectory (due to FFP local switching) over a spherical trajectory so that the overall heating is effectively more focused into the centre. Any non-intentional remagnetization processes that are leading to those additional heating effects on the circular trajectory would thereby be effectively duty-cycled so that the average heat generation at such a specific location will be smaller.

It is important to note that at the location of the FFP there may be some heating effect (due to Neel rotation of magnetic material there, only if present). However, according to the present invention the heating within the circle/sphere that is formed by the trajectory of the FFP, i.e. at the location of the tumor, will be substantially more effective. The latter heating effect is due to Brownian rotation of the particles. The fact that additional heating occurs at the FFP location and trajectory is actually beneficial since it will suppress the heat leakage from the central tumor location.

A specific example here could be the use of two contrast agents simultaneously. The first agent could be a standard blood pool agent for MPI in imaging mode, injected intravenously, whereas the second one is e.g. administered intratumorally, for treatment. The first agent will be present and may even slightly accumulate in or in the vicinity of the tumor, to highlight the position of the tumor, whereas the second one is within the time frame of the treatment fixed within the tumor. It is important in this case that any heating due to material of the first agent is kept to a minimum.

It is preferred that the magnetic particles should essentially be unbound. This means that particles that are fixed to e.g. cells (active targeting) may have limited heating ability. However, free moving particles, or particles that are contained in liposomes or emulsions will have superior heating power provided that the viscosity of the medium in which the particles are located is equal or similar to that of water.

Another important effect due to the change of modus operandi (Brownian rotation rather than Neel rotation) is that due to the polydispersity of magnetic material (as it usually comes after chemical synthesis), Brownian rotation is not specifically bound to a size—frequency combination for effective heating. The graphs shown in FIGS. 9 and 10 give a small explanation.

Figure 9:
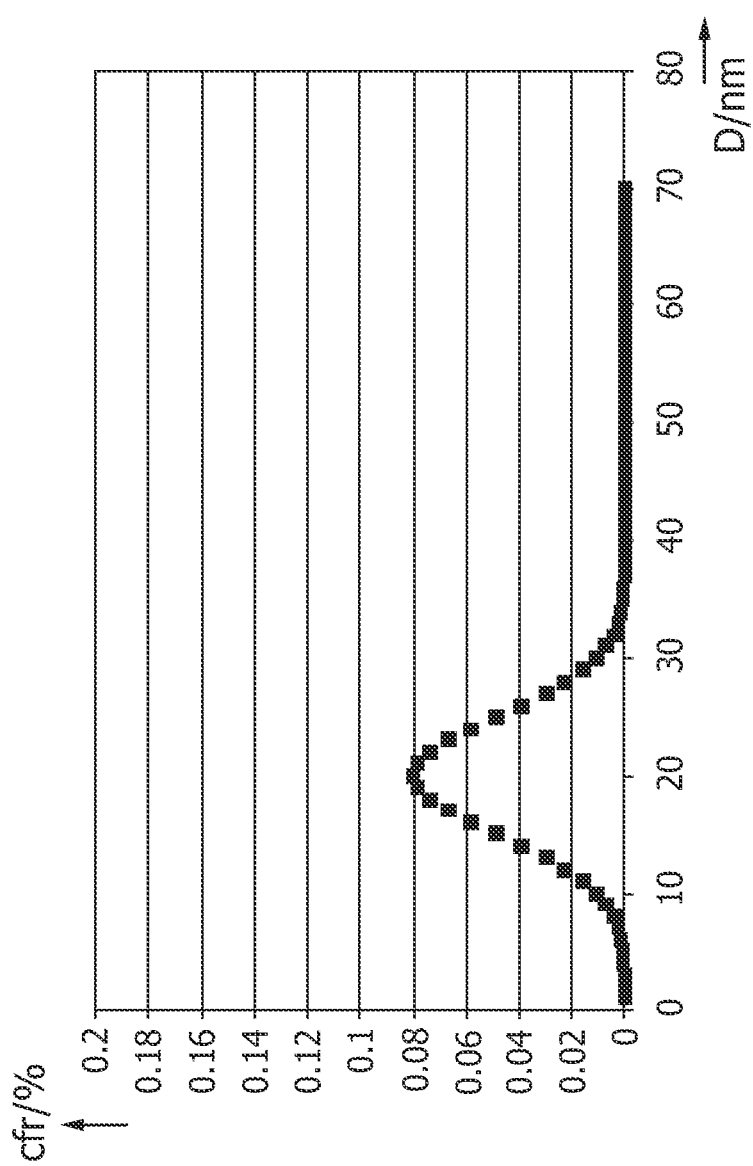
FIG. 9 shows a diagram illustrating a Gaussian distribution of a polydisperse material.

Assumed is a Gaussian distribution of a polydisperse material as shown in FIG. 9 illustrating fractional distribution versus magnetic core diameter, with average 20 nm and standard deviation 5 nm. The X-axis shows the magnetic core diameter D in nanometer; the Y-axis shows the intensity of distribution or fraction (cfr %). The integral under this distribution should be equal to 1=100%.

Figure 10:
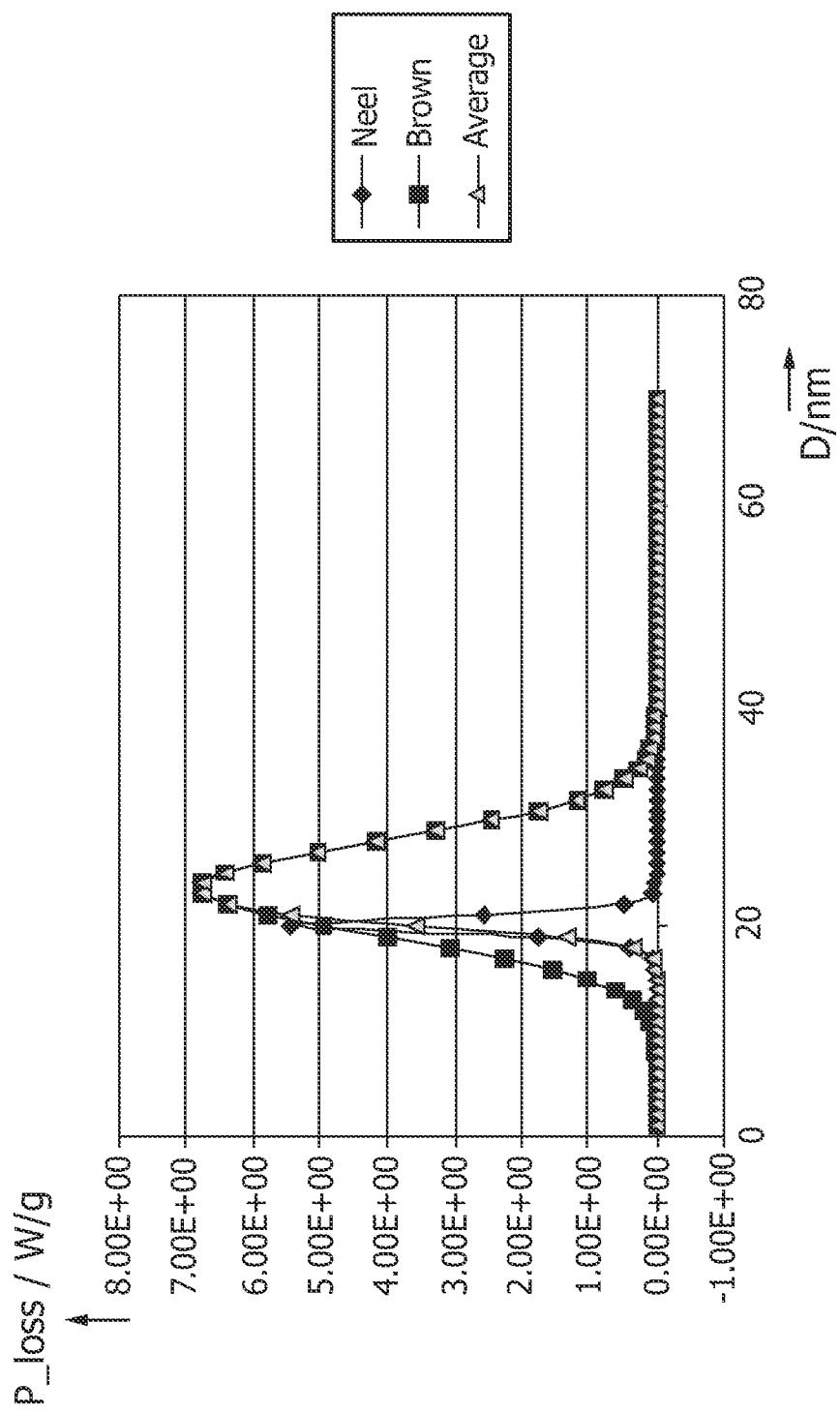
FIG. 10 shows a diagram illustrating power generation as function of magnetic core diameter.

FIG. 10 shows a diagram illustrating power generation as function of magnetic core diameter. X-axis shows the magnetic core diameter D; the Y-axis shows the fractional power loss per unit density $P_{loss}$, calculated from the product of the power loss per unit density (W/g) and the intensity of distribution for a given magnetic core diameter. The integral under the curve gives the total power loss per unit density (W/g) for a material. The three curves correspond to Neel-only, Brown-only and a combination thereof (average). The term average relates to the weighing of the time constants for Neel and Brown in the latter case $\tau_{eff} = \tau_N \tau_B/(\tau_N + \tau_B)$.

If it is integrated over all the material, the integrated power density for the complete magnetic material in the case of Brownian rotation is about an order of magnitude higher than that of Neel, i.e. 76 W/g versus 11 W/g—to be compared to 62 W/g average [saturation magnetization Ms=230 kA/m/magnetic field H=10 kA/m].

Fundamental equations, that can also be found in 'Magnetism in Medicine', Chapter 4.6/Rosensweig 2002, JMMM 252, 370-74, are:

The loss power density of magnetic material per unit weight material is given by (in linear approximation): $P_{N/B} = \mu_0 \pi \chi'' H^2 f/\rho$ which is a function of frequency f and applied field H. The equation is scaled by the density of the material.

The imaginary part of the susceptibility is given by $$\chi''_{N/B} = \chi_0 \frac{\vartheta}{1+\vartheta^2}$$

$$\vartheta_{N/B} = f\tau_{N/B}$$

$$\chi_0 = \mu_0 M_S^2 \frac{V_i}{kT}$$

where the volume $V_i$ is indicative for the magnetic core volume on which a magnetic torque is exerted.

The fundamental time constants for Neel and Brown—separately—are given by $$\tau_N = \tau_0 \exp\frac{KV_i}{kT}$$

$$\tau_B = 4\pi\eta\frac{Vh_i}{kT}$$

respectively.

It is to be noted are the magnetic anisotropy K, viscosity $\eta$ and a hydrodynamic volume $Vh_i$ including dimensions of the magnetic core and the coating.

For both modes simultaneously the time constant can be calculated as $\tau_{eff} = \tau_N \tau_B/(\tau_N + \tau_B)$. Other equations hold.

The present invention can be favourably applied in magnetic hyperthermia or thermoablation for treatment of different cancers in e.g. prostate, breast or head/neck. It can also be applied in combination with other cancer treatment options such as brachy, chemo, radiation etc.

From literature such procedures typically go from minutes to tens of minutes. Most important is the application as hyperthermia, where two fundamental modes exist. Either one aims for moderate heating at elevated temperature of 41°-43° C., during which hyperthermia is primarily meant to assist other treatment for better efficacy, or one aims for thermo-ablation at 45°-47° C., resulting in direct cell death or apoptosis with the risk of heating surrounding healthy tissue. Therefore for the latter case a fast temperature transient would be most appropriate. The simple answer on 'how long' would be as long as the treatment does require this elevated temperature. For instance, to support local brachytherapy (prostate) 1-hour fractions were used, to be repeated weekly. It is expected focal therapy to go to high temperature and therefore shorter duration with possibly more fractionation of the treatment. Important to treatment planning would be the SAR (specific absorption rate) that may limit the time. The SAR will be restricted to where magnetic material is modulated. The use of MPI and in particular the present invention will be beneficial to this extend, so that a longer treatment time would be possible compared to full-body modulating magnetic fields.

In summary, according to the present invention a family of revolving focal heating sequences for MPI are proposed that allow for a very local heating for focal cancer therapy. The invention relies primarily on the Brownian rotational degree of freedom of suspended magnetic particles. Given that magnetic particles are delivered intratumorally, a sequence can be designed that is able to rotate the cumulative magnetic vector in a particular area in a concerted way. Such a fundamentally 3D sequence must be revolving around the defined area in which magnetic particles are present and where eventually the heating effect will be focused. Heating power will scale with the revolving frequency of the particles.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An arrangement (10) for heating of a magnetic material (100) located in the centre region of an inscribed sphere within a region of action, which arrangement comprises:

selection means (210) for generating a magnetic selection field (211) having a pattern in space of its magnetic field strength such that a first sub-zone (301) having a low magnetic field strength and a second sub-zone (302) having a higher magnetic field strength are formed in the region of action (300), drive means (220) for changing the position in space of the two sub-zones (301, 302) in the region of action (300) by means of a magnetic drive field (221) so that the magnetization of the magnetic material (100) changes locally, and control means (76) for controlling the drive means (220) to change the position in space of the first sub-zone (301) along a sequence of locations around said inscribed sphere for so long and with such a frequency that the centre region of said inscribed sphere is heated.

2. An arrangement (10) as claimed in claim 1, wherein said control means (76) is adapted for controlling the drive means (220) to change the position in space of the first sub-zone (301) along a two-dimensional sequence of locations on a circle, around said inscribed sphere.

3. An arrangement (10) as claimed in claim 1, wherein said control means (76) is adapted for controlling the drive means (220) to change the position in space of the first sub-zone (301) along a three-dimensional sequence of locations on a sphere, around said inscribed sphere.

4. An arrangement (10) as claimed in claim 1, wherein said control means (76) is adapted for controlling the drive means (220) to change the position in space of the first sub-zone (301) with constant angular velocity.

5. An arrangement (10) as claimed in claim 1, wherein said control means (76) is adapted for controlling the drive means (220) to change the position in space of the first sub-zone (301) with a frequency in the range from 1 to 100 kHz.

6. An arrangement (10) as claimed in claim 1, further comprising:
receiving means (230) for acquiring detection signals, which detection signals depend on the magnetization in the region of action (300), which magnetization is influenced by the change in the position in space of the first and second sub-zone (301, 302), and processing means (74) for reconstructing an image of at least the centre region from the acquired detection signals.

7. An arrangement (10) as claimed in claim 1, wherein magnetic material (100) comprises monodomain magnetic nanoparticles.

8. An arrangement (10) as claimed in claim 1, wherein magnetic material (100) comprises monodomain magnetic nanoparticles encapsulated into liposomes, polymersomes or vesicles having an inner volume with viscosity equal or similar to that of water and separated by a hydrophobic membrane, wherein the magnetic particles are arranged in the inner volume.

9. An arrangement (10) as claimed in claim 1, wherein said control means (76) is adapted for controlling the drive means (220) to change the position in space of the first sub-zone (301) with a frequency in the range from 10 to 30 kHz.

10. An arrangement (10) as claimed in claim 1, wherein magnetic material (100) comprises colloidally stabilised monodomain magnetic nanoparticles encapsulated into liposomes, polymersomes or vesicles having an inner volume with viscosity equal or similar to that of water, and separated by a hydrophobic membrane, wherein the magnetic particles are arranged in the inner volume.

* * * * *